United States Patent [19]

Ollinger

[11] 4,315,870
[45] Feb. 16, 1982

[54] PHOSPHORODIAMIDOTHIOATES

[75] Inventor: Janet Ollinger, Chalfont, Pa.

[73] Assignee: Rohm and Haas Company, Philadelphia, Pa.

[21] Appl. No.: 102,471

[22] Filed: Dec. 11, 1979

Related U.S. Application Data

[63] Continuation-in-part of Ser. No. 5,937, Jan. 24, 1979, and Ser. No. 42,689, May 25, 1979.

[51] Int. Cl.$^3$ .................... C07F 9/24; A01N 57/28; A01N 57/30
[52] U.S. Cl. .................... 260/947; 260/959; 260/941; 260/943; 260/944; 260/945; 260/949; 260/951; 260/952; 260/940; 260/948; 260/950; 260/955; 424/220
[58] Field of Search .................... 260/909, 959, 947

[56] References Cited

U.S. PATENT DOCUMENTS

| | | | |
|---|---|---|---|
| 3,207,661 | 9/1965 | Curtis et al. | 71/87 |
| 3,317,637 | 5/1967 | Brust | 260/959 |
| 3,324,204 | 6/1967 | Tolkmith | 260/959 |
| 3,397,270 | 8/1968 | Hamm | 424/220 |
| 3,399,213 | 8/1968 | Osborne | 260/326 |
| 3,484,469 | 12/1969 | Guinet et al. | 260/444.2 |
| 3,504,086 | 3/1970 | Aichenegg | 424/219 |
| 3,511,635 | 5/1970 | Braxton et al. | 71/87 |
| 3,626,039 | 12/1971 | Hoffmann | 260/959 |
| 3,666,842 | 5/1972 | Aichenegg | 260/959 |
| 3,716,600 | 2/1973 | Magee | 260/959 |
| 3,760,043 | 9/1973 | Kishino et al. | 260/959 |
| 3,773,861 | 11/1973 | Hofer et al. | 260/959 |
| 3,825,634 | 7/1974 | Magee | 260/956 |
| 3,845,172 | 10/1974 | Magee | 260/956 |
| 3,885,032 | 5/1975 | Magee | 424/212 |
| 3,914,417 | 10/1975 | Magee | 424/219 |
| 3,975,523 | 8/1976 | Hoffmann et al. | 424/212 |
| 4,020,161 | 4/1977 | Gutman | 424/211 |
| 4,049,679 | 9/1977 | Magee | 424/212 |
| 4,110,443 | 8/1978 | Magee | 424/212 |

FOREIGN PATENT DOCUMENTS 2114885 10/1972 Fed. Rep. of Germany .
491647 11/1975 U.S.S.R. .

OTHER PUBLICATIONS

Abstract Japanese Patent 77012251.
Abstract Russian Patent 213,844.
Abstract Russian Patent 300,471-S.
Abstract Russian Patent 216,724.
Abstract Russian Patent 463,677.
Fest et al, "The Chemistry of Organophosphorus Pesticides", (1973) p. 190 etc.

Primary Examiner—Anton H. Sutto

[57] ABSTRACT

Disclosed are compounds of the formula:

$$R^1-\overset{X}{\underset{\parallel}{C}}-N\diagup\overset{R^5}{\underset{\diagdown P \diagup}{\diagdown}}NR^3R^4 \atop X^1 \diagdown SR^2$$

wherein
R$^1$ is
  a hydrogen atom;
  an unsubstituted or substituted alkyl group;
  an alkynyl group;
  an alkenyl group;
  an alkyldienyl;
  a cycloalkyl group;
  an alkoxycarbonyl group;
  an unsubstituted or substituted phenyl group;
  an unsubstituted or substituted phenylalkyl group;
R$^2$ is an unsubstituted alkyl group;
R$^3$ is a hydrogen atom, an alkyl group, or an alkenyl group;
R$^4$ is a hydrogen atom, an alkyl group or additionally when R$^3$ and R$^5$ are not taken together to form a heterocycle, an alkenyl group;
R$^5$ is
  a hydrogen atom;
  an unsubstituted or substituted alkyl group;
  an alkynyl group;
  an alkenyl group;
  a cycloalkyl group;
  an unsubstituted or substituted phenyl group;
  an unsubstituted or substituted phenyl (C$_1$–C$_5$) alkyl group, or
R$^3$ and R$^5$ can be taken together to form a heterocyclic ring of the formula $$R^1-\overset{X}{\underset{\parallel}{C}}-N\diagup\overset{Z}{\underset{\diagdown P \diagup}{\diagdown}}N-R^4 \atop X^1 \diagdown SR^2$$

wherein Z is a —CH$_2$CH$_2$— group, a —CH$_2$CH$_2$CH$_2$— group, or a —CH$_2$CH$_2$CH$_2$CH$_2$— group; and
X and X$^1$ are independently an oxygen atom or a sulfur atom;
as well as compositions containing them, and to methods of using them to control certain harmful pests.

10 Claims, No Drawings

PHOSPHORODIAMIDOTHIOATES

This is a continuation-in-part of application Ser. No. 005,937 filed Jan. 24, 1979 and No. 042,689 filed May 25, 1979.

This invention relates to novel phosphorodiamidothioates, to compositions containing them, and to methods of using them to control a variety of harmful pests.

The novel compounds of this invention can be represented by the formula

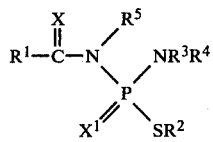

(I)

wherein $R^1$ is a hydrogen atom;

an unsubstituted ($C_1$–$C_{12}$) alkyl group, preferably ($C_1$–$C_6$), more preferably ($C_1$–$C_4$), most preferably methyl or ethyl;

a ($C_1$–$C_{12}$) alkyl group, substituted with up to three substituents selected from chloro, bromo, or fluoro, preferably a ($C_1$–$C_6$) group substituted with up to three substituents selected from chloro, bromo, and fluoro, more preferably trifluoromethyl;

a ($C_1$–$C_{12}$) alkyl group substituted with one substituent selected from cyano, nitro, ($C_1$–$C_6$)alkoxy, ($C_1$–$C_6$)alkylthio, ($C_1$–$C_6$) alkylsulfinyl, ($C_1$–$C_6$) alkylsulfonyl, ($C_1$–$C_6$) alkylcarbonyl, ($C_1$–$C_6$) alkoxycarbonyl, ($C_1$–$C_6$) alkylcarbonyloxy, ($C_1$–$C_6$) mono- or dialkylaminocarbonyl, phenoxy, phenylthio, phenylsulfinyl, phenylsulfonyl, phenylcarbonyl, phenoxycarbonyl, phenylcarbonyloxy, phenylaminocarbonyl, ($C_3$–$C_6$) alkenyloxycarbonyl, ($C_3$–$C_6$) alkenylcarbonyloxy, aminocarbonyl, and ($C_1$–$C_6$) alkylcarbonylamino groups, preferably a ($C_1$–$C_6$)alkyl group substituted with one substituent selected from cyano, nitro, ($C_1$–$C_4$)alkoxy, ($C_1$–$C_4$)alkylthio, ($C_1$–$C_4$)alkylsulfinyl, ($C_1$–$C_4$)alkylsulfonyl, acetyl, ($C_1$–$C_4$)alkoxycarbonyl, ($C_1$–$C_4$)alkylcarbonyloxy, ($C_1$–$C_4$) mono- or dialkylaminocarbonyl, phenoxy, phenylthio, phenylsulfinyl, phenylsulfonyl, phenylcarbonyl, phenoxycarbonyl, phenylcarbonyloxy, phenylaminocarbonyl, ($C_3$–$C_4$)alkenyloxycarbonyl, ($C_3$–$C_4$)alkenylcarbonyloxy, aminocarbonyl, and ($C_1$–$C_4$)alkylcarbonylamino groups; more preferably a ($C_1$–$C_4$)alkyl group substituted with one substituent selected from cyano, nitro, methoxy, methylthio, methylsulfinyl, methylsulfonyl, acetyl, methoxycarbonyl, ethoxycarbonyl, methylcarbonyloxy, mono- or dimethylaminocarbonyl, phenoxy, phenylthio, phenylsulfinyl, phenylsulfonyl, phenylcarbonyl, phenoxycarbonyl, phenylcarbonyloxy, phenylaminocarbonyl, ($C_3$–$C_4$) alkenyloxycarbonyl, ($C_3$–$C_4$) alkenylcarbonyloxy, aminocarbonyl, and methylcarbonylamino groups;

a ($C_3$–$C_{12}$)alkynyl group, preferably ($C_3$–$C_6$), more preferably ($C_3$–$C_4$);

a ($C_2$–$C_{12}$)alkenyl group, preferably ($C_3$–$C_6$), more preferably ($C_3$–$C_4$);

a ($C_4$–$C_{17}$) alkyldienyl group;

a ($C_3$–$C_6$)cycloalkyl group;

a ($C_1$–$C_6$) alkoxycarbonyl group, preferably ($C_1$–$C_4$), more preferably ($C_1$–$C_2$);

an unsubstituted phenyl group;

an unsubstituted phenyl ($C_1$–$C_5$) alkyl group, preferably phenyl ($C_1$–$C_3$) alkyl, more preferably benzyl;

a phenyl or phenyl ($C_1$–$C_5$) alkyl group, preferably phenyl ($C_1$–$C_3$) alkyl, more preferably benzyl substituted with up to three substituents selected from cyano, nitro, halogen, ($C_1$–$C_6$)alkyl, ($C_1$–$C_6$)alkoxy, ($C_1$–$C_6$) alkylthio, ($C_1$–$C_6$) alkylsulfinyl, ($C_1$–$C_6$) alkylsulfonyl, phenoxy, ($C_1$–$C_6$)haloalkyl, trifluoromethyl, ($C_1$–$C_6$)mono- or dialkylaminocarbonyl, ($C_1$–$C_6$)alkoxycarbonyl, ($C_1$–$C_6$) alkylcarbonyl, ($C_1$–$C_6$)alkylcarbonyloxy, phenylthio, phenylsulfinyl, phenylsulfonyl, benzyl, phenylcarbonyl, phenoxycarbonyl, phenylcarbonyloxy, phenylaminocarbonyl, ($C_3$–$C_6$)alkenyloxycarbonyl, ($C_3$–$C_6$)alkenylcarbonyloxy, aminocarbonyl, and ($C_1$–$C_6$) alkylcarbonylamino groups; preferably a phenyl group substituted with up to three substituents selected from cyano, nitro, methyl, methoxy, phenoxy, acetoxy, acetyl, trifluoromethyl, chloro, fluoro, bromo, methylthio, methylsulfinyl, methylsulfonyl;

$R^2$ is a ($C_2$–$C_6$)alkyl group, preferably ($C_2$–$C_4$), more preferably ($C_3$–$C_4$);

$R^3$ is a hydrogen atom, a ($C_1$–$C_3$) alkyl group, preferably methyl or ethyl, more preferably methyl or a ($C_3$–$C_6$) alkenyl group, preferably propenyl;

$R^4$ is a hydrogen atom, a ($C_1$–$C_3$) alkyl group, preferably methyl or ethyl, more preferably methyl, or additionally when $R^3$ or $R^5$ are not taken together to form a heterocycle, a ($C_3$–$C_6$) alkenyl group preferably propenyl;

$R^5$ is a hydrogen atom; an unsubstituted ($C_1$–$C_{12}$) alkyl group, preferably ($C_1$–$C_6$) more preferably ($C_1$–$C_4$), most preferably methyl or ethyl;

a ($C_1$–$C_{12}$) alkyl group substituted with one substituent selected from cyano, nitro, ($C_1$–$C_6$)alkoxy, ($C_1$–$C_6$)alkylthio, ($C_1$–$C_6$)alkylsulfinyl, ($C_1$–$C_6$) alkylsulfonyl, ($C_1$–$C_6$) alkylcarbonyl, ($C_1$–$C_6$) alkylcarbonyloxy, ($C_1$–$C_6$) mono- or dialkylaminocarbonyl, phenoxy, phenylthio, phenylsulfinyl, phenylsulfonyl, phenylcarbonyl, phenoxycarbonyl, phenylcarbonyloxy, phenylaminocarbonyl, ($C_3$–$C_6$) alkenyloxycarbonyl, ($C_3$–$C_6$) alkenylcarbonyloxy, aminocarbonyl, and ($C_1$–$C_6$) alkylcarbonylamino groups, preferably a ($C_1$–$C_6$) alkyl group substituted with one substituent selected from cyano, nitro, ($C_1$–$C_4$)alkoxy, ($C_1$–$C_4$)alkylthio, ($C_1$–$C_4$)alkylsulfinyl, ($C_1$–$C_4$)alkylsulfonyl, acetyl, ($C_1$–$C_4$)alkoxycarbonyl, ($C_1$–$C_4$)alkylcarbonyloxy, ($C_1$–$C_4$)mono- or dialkylaminocarbonyl, phenoxy, phenylthio, phenylsulfinyl, phenylsulfonyl, phenylcarbonyl, phenoxycarbonyl, phenylcarbonyloxy, phenylaminocarbonyl, ($C_3$–$C_4$)alkenyloxycarbonyl, ($C_3$–$C_4$)alkenylcarbonyloxy, aminocarbonyl, and ($C_1$–$C_4$)alkylcarbonylamino groups; more preferably a ($C_1$–$C_4$)alkyl group substituted with one substituent selected from cyano, nitro, methoxy, methylthio, methylsulfinyl, methylsulfonyl, acetyl, methoxycarbonyl, ethoxycarbonyl, methylcarbonyloxy, mono- or dimethylaminocarbonyl, phenoxy, phenylthio, phenylsulfinyl, phenylsulfonyl, phenylcarbonyl, phenoxycarbonyl, phenylcarbonyloxy, phenylaminocarbonyl, ($C_3$–$C_4$) alkenyloxycarbonyl, ($C_3$–$C_4$) alkenylcarbonyloxy, aminocarbonyl, and methylcarbonylamino groups;

a ($C_3$–$C_{12}$)alkynyl group, preferably ($C_3$–$C_6$), more preferably ($C_3$–$C_4$);

a ($C_3$–$C_{12}$)alkenyl group, preferably ($C_3$–$C_6$), more preferably ($C_3$–$C_4$);

a ($C_3$–$C_6$)cycloalkyl group, preferably ($C_5$–$C_6$);

an unsubstituted phenyl group;

an unsubstituted phenyl ($C_1$–$C_5$) alkyl preferably phenyl ($C_1$–$C_3$) alkyl; more preferably benzyl;

a phenyl or a phenyl ($C_1$–$C_5$) alkyl group substituted with up to three substituents selected from cyano, nitro, halogen, ($C_1$–$C_6$)alkyl, ($C_1$–$C_6$)alkoxy, ($C_1$–$C_6$) alkylthio, ($C_1$–$C_6$) alkylsulfinyl, ($C_1$–$C_6$) alkylsulfonyl, phenoxy, ($C_1$–$C_6$)haloalkyl, trifluoromethyl, ($C_1$–$C_6$)mono- or dialkylaminocarbonyl, ($C_1$–$C_6$)alkoxycarbonyl, ($C_1$–$C_6$) alkylcarbonyl, ($C_1$–$C_6$)alkylcarbonyloxy, phenylthio, phenylsulfinyl, phenylsulfonyl, benzyl, phenylcarbonyl, phenoxycarbonyl, phenylcarbonyloxy, phenylaminocarbonyl, ($C_3$–$C_6$)alkenyloxycarbonyl, ($C_3$–$C_6$)alkenylcarbonyloxy, aminocarbonyl, or ($C_1$–$C_6$) alkylcarbonylamino groups; preferably a phenyl group substituted with up to three substituents selected from cyano, nitro, methyl, methoxy, phenoxy, acetoxy, acetyl, trifluoromethyl, chloro, fluoro, bromo, methylthio, methylsulfinyl, methylsulfonyl;

$R^3$ and $R^5$ can be taken together to form a heterocyclic ring of the formula

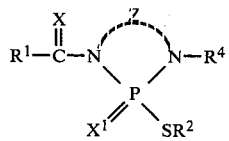

wherein Z is a —$CH_2CH_2$— group, a —$CH_2CH_2CH_2$— group, or a $CH_2CH_2CH_2CH_2$ group, preferably a —$CH_2CH_2$— group, or a —$CH_2CH_2CH_2$— group; and X and $X^1$ are independently an oxygen atom or a sulfur atom, preferably an oxygen atom.

As used in the specification and claims, the terms alkyl, alkenyl and alkynyl are meant to include branched as well as straight chain alkyl, alkenyl and alkynyl groups. Representative examples of such groups include methyl, ethyl, propyl, isopropyl, sec-butyl, isobutyl, tert-butyl, pentyl, neopentyl, hexyl, allyl, 2-butenyl, 3-methyl-1-pentenyl, 3-hexenyl, propynyl, 1-pentynyl, 4-methyl-1-pentynyl, hexynyl, and the like.

By a substituted phenyl, as used in the specification and claims, is meant phenyl group substituted with one or more, but preferably with one to three, substituents selected from cyano, nitro, halogen, alkyl, alkoxy, alkylthio, alkylsulfinyl, alkylsulfonyl, phenoxy, haloalkyl, trifluoromethyl, mono- or dialkylaminocarbonyl, alkoxycarbonyl, alkylcarbonyl, alkylcarbonyloxy, phenylthio, phenylsulfinyl, phenylsulfonyl, benzyl, phenylcarbonyl, phenoxycarbonyl, phenylcarbonyloxy, phenylaminocarbonyl, alkenyloxycarbonyl, alkenyl carbonyloxy, aminocarbonyl and alkylcarbonylamino and the like, wherein each alkyl moiety is straight or branched chain and contains from 1 to 6, preferably from 1 to 4, more preferably 1 or 2 carbon atoms.

By a substituted alkyl group as used in the specification and claims is meant a ($C_1$–$C_{12}$) alkyl group, preferably ($C_1$–$C_6$), more preferably ($C_1$–$C_4$), substituted with up to three substituents selected from halogen; or one substituent selected from cyano, nitro, alkoxy, alkylthio, alkylsulfinyl, alkylsulfonyl, alkylcarbonyl, alkoxycarbonyl, alkylcarbonyloxy, mono- or dialkylaminocarbonyl, alkylcarbonylamino, and the like, wherein each alkyl moiety is straight or branched chain, and contains from 1 to 6, preferably from 1 to 4, more preferably 1 to 2, most preferably 1 carbon atom(s); alkenyloxycarbonyl and alkenylcarbonyloxy wherein the alkenyl moiety contains from 3 to 6 preferably from 3 to 4 carbon atoms; and phenoxy, phenylthio, phenylsulfinyl, phenylsulfonyl, phenylcarbonyl, phenyloxycarbonyl, phenylcarbonyloxy, phenylaminocarbonyl, and the like, wherein the phenyl is optionally substituted (but preferably unsubstituted) with substituents such as defined above for substituted phenyl; and aminocarbonyl.

By an alkenyl group, as used in the specification and claims, is meant an alkenyl group such as an allyl group, or the like, with one cis or trans double bond, or a styryl group.

By an alkynyl group, as used in the specification and claims, is meant an alkynyl group, such as a propargyl group, with one triple bond.

By a substituted phenylalkyl group is meant an phenylalkyl group e.g., benzyl, phenethyl, 3-phenyl-1-methylpropyl, etc., the aromatic ring of which is substituted with one or more, but preferably with one to three substituents selected from the group of substituents defined for substituted phenyl above.

By an alkyldienyl, as used in the specification and claims, is meant a diene such as 2,4-pentadienyl group with either cis or trans double bonds which can be either conjugated or isolated.

By an acyl group as used in the specification and claims is meant a group of the formula RC(X) wherein R is a hydrogen atom or an organic group and X is an oxygen or sulfur atom.

By a "B" ring as used in the specification and claims is meant the benzene ring of the fused benzene and pyridine ring system of quinoline or isoquinoline.

The most preferred compounds of this invention possess especially enhanced nematocidal, acaricidal, fungicidal and arthropodicidal, particularly nematocidal, acaricidal and insecticidal activity. They can be represented by the formula:

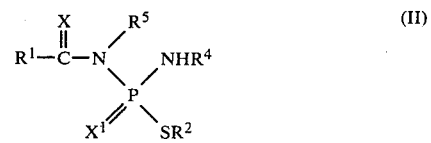

(II)

wherein $R^1$ is a hydrogen atom, methyl group, ethyl group, methoxymethyl group, a cyclopropyl group or a trifluoromethyl group;

$R^2$ is a ($C_3$–$C_4$)alkyl group;

$R^4$ is a methyl group;

$R^5$ is a hydrogen atom, a methyl or ethyl group, preferably methyl; and

X and $X^1$ are independently a sulfur or an oxygen atom, preferably oxygen.

Particular preferred compounds have the following formulas:

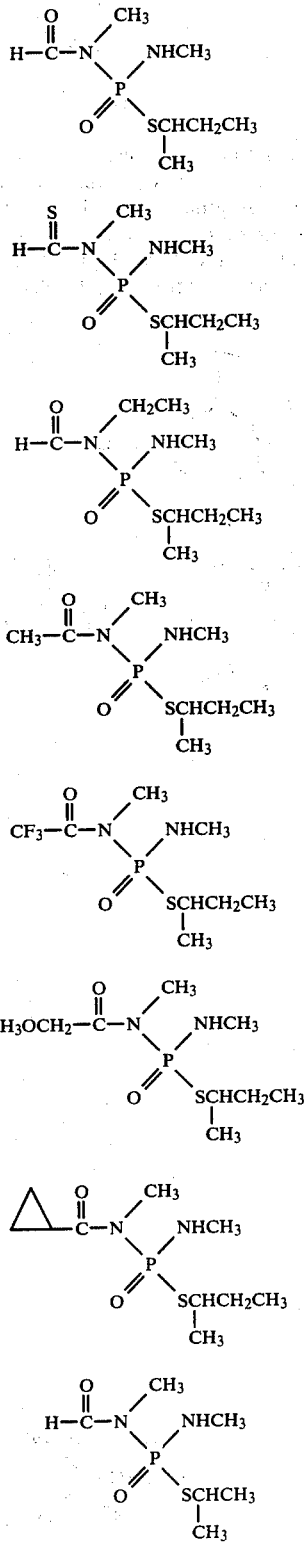

Typical examples of compounds within the scope of this invention include the following:

N-Ethyl N'-methyl N-methylcarbonyl S-(1-methylpropyl) phosphorodiamidothioate

N-Hexyl N-hexylcarbonyl N',N'-dimethyl S-propyl phosphorodiamidothioate

N-Hydrogencarbonyl N,N'-dimethyl S-ethyl phosphorodiamidothioate

N,N'-Diethyl N-ethylcarbonyl S-(2-methylpropyl) phosphorodiamidothioate

N-Ethylcarbonyl N,N'-dimethyl S-(1-methylethyl) phosphorodiamidothioate

N,N'-Diethyl N-hydrogencarbonyl S-propyl phosphorodiamidothioate

N-Hydrogencarbonyl N,N'-dipropyl S-(1-methylpropyl) phosphorodiamidothioate

S-Butyl N',N'-diethyl N-methylcarbonyl N-propyl phosphorodiamidothioate

N-Dodecylcarbonyl N,N'-dimethyl S-propyl phosphorodiamidothioate

N-Chloromethylcarbonyl N,N'-diethyl S-(1-methylpropyl) phosphorodiamidothioate

N-Hydrogencarbonyl N',N'-dimethyl S-hexyl N-propyl phosphorodiamidothioate

N-Hydrogencarbonyl S-hexyl N',N'-dimethyl N-(3-methylsulfonylpropyl) phosphorodiamidothioate N',N'-Diethyl N-methylcarbonyl S-(2-methylpropyl) N-(2-propenyl) phosphorodiamidothioate N-(2-Cyanoethyl) S-ethyl N-ethylcarbonyl N',N'-dimethyl phosphorodiamidothioate N-(2-Butynyl) N-hydrogencarbonyl N',N'-dimethyl S-propyl phosphorodiamidothioate N-(2-Methoxyethyl) N',N'-dimethyl N-methylcarbonyl S-propyl phosphorodiamidothioate N',N',S-Triethyl N-hydrogencarbonyl N-(2-methylthioethyl) phosphorodiamidothioate N-(2-Ethoxycarbonylethyl) N'-ethyl N-hydrogencarbonyl S-(2-methylbutyl)phosphorodiamidothioate N-Cyclohexyl N',N',S-triethyl N-methylcarbonyl phosphorodiamidothioate N-(2-Propenylcarbonyl) N,N',N',S-tetrapropyl phosphorodiamidothioate N-(3-Dodecenyl)carbonyl N',N'-diethyl S-pentyl N-propyl phosphorodiamidothioate S-Hexyl N-(2-hexenylcarbonyl) N',N',N-trimethyl phosphorodiamidothioate N,N'-Diethyl N-(2-propynylcarbonyl) S-propyl phosphorodiamidothioate S-Butyl N-(3-hexynyl)carbonyl N-pentyl N',N'-dipropyl phosphorodiamidothioate N-Cyclopropylcarbonyl N,S-diethyl N',N'-dimethyl phosphorodiamidothioate N-Cyclohexylcarbonyl N,N'-dimethyl S-pentyl phosphorodiamidothioate N,N'-Diethyl N-phenylcarbonyl S-propyl phosphorodiamidothioate N-Benzylcarbonyl N,N',S-tripropyl phosphorodiamidothioate S-Ethyl N,N'-dimethyl N-(5-phenylpentyl)carbonyl phosphorodiamidothioate N,N'-Dimethyl S-(1-methylpropyl) N-(4-nitrophenyl)carbonyl phosphorodiamidothioate N-Dodecylthiocarbonyl N,N'-diethyl S-propyl phosphorodiamidothioate N-Hexylthiocarbonyl N,N'-dimethyl S-propyl phosphorodiamidothioate N-[(2-Ethoxycarbonylpropyl)carbonyl] N,N'-dimethyl S-(1-methylpropyl) phosphorodiamidothioate N,N′-Diethyl N-(2-methoxyethylcarbonyl) S-propyl phosphorodiamidothioate N-Hydrogenthiocarbonyl N,N′-dimethyl S-(1-methylpropyl) phosphorodiamidothioate N,N′-Dimethyl S(1-methylpropyl) N-trifluoromethylthiocarbonyl phosphorodiamidothioate N,N′-Dimethyl N-methylthiocarbonyl S-propyl phosphorodiamidothioate N,N′-Dimethyl S-propyl N-propylthiocarbonyl phosphorodiamidothioate N-Methylthiomethylthiocarbonyl N,N′,S-tripropyl phosphorodiamidothioate N-Cyanomethylcarbonyl N,N′-dimethyl S-(1-methylpropyl) phosphorodiamidodithioate N-(4-Nitrophenylcarbonyl) N,N′,S-tripropyl phosphorodiamidodithioate N-Hexylcarbonyl N,N′-dimethyl S-(2-methylpropyl) phosphorodiamidodithioate N-Cyclopropylcarbonyl N,N′-dimethyl S-(1-methylpentyl) phosphorodiamidodithioate N,N′-(1,2-Ethanediyl) N-hydrogencarbonyl S-(1-methylpropyl)phosphorodiamidothioate N,N′-(1,2-Ethanediyl) N-methylcarbonyl S-(1-methylethyl) phosphorodiamidothioate N-Chloromethylcarbonyl N,N′-(1,2-propanediyl) S-propyl phosphorodiamidothioate S-Ethyl N-methoxymethylcarbonyl N-(1,3-propanediyl) phosphorodiamidothioate N-Hydrogencarbonyl N,N′-(1,3-propanediyl) S-propyl phosphorodiamidothioate The compounds of the present invention can be prepared by a variety of methods.

One method involves acylation of an N,N′-di- or tri-substituted S-alkyl phosphorodiamidothioate. For example:

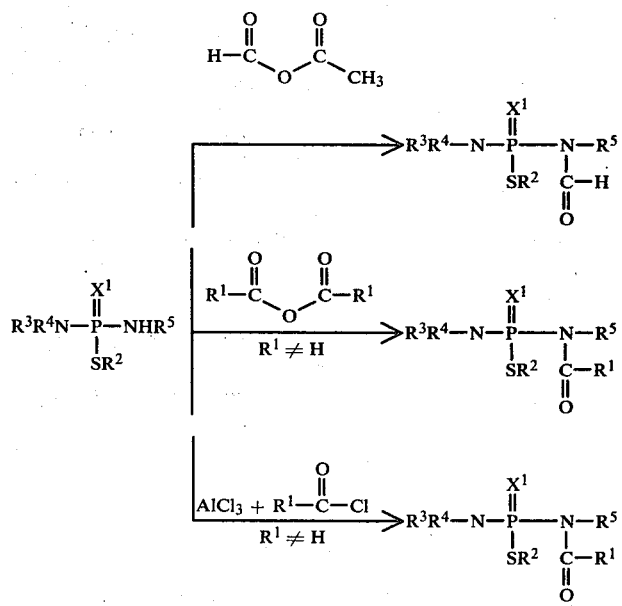

wherein $R^1$, $R^2$, $R^3$, $R^4$ and $R^5$ are as defined for Formula I.

Another method where $R^1$=H or unsubstituted alkyl involves the hydrolysis of a formamidine. The general reaction can be represented by the following equation:

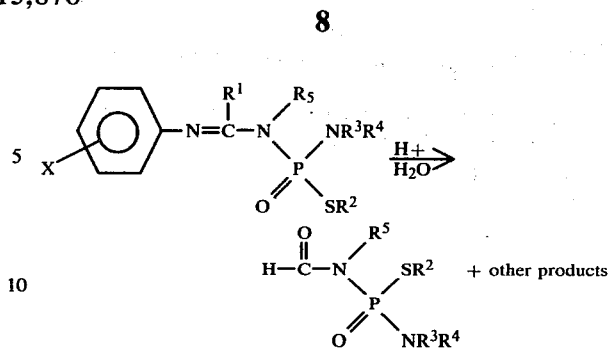

A third method of preparation, when $R^1 \neq$ hydrogen, involves the reaction of acyl halides with substituted or unsubstituted pyridines and the appropriate phosphorodiamidothioate. The reaction proceeds through the intermediacy of an N-acylpyridinium salt. The general reaction can be represented by the following equation:

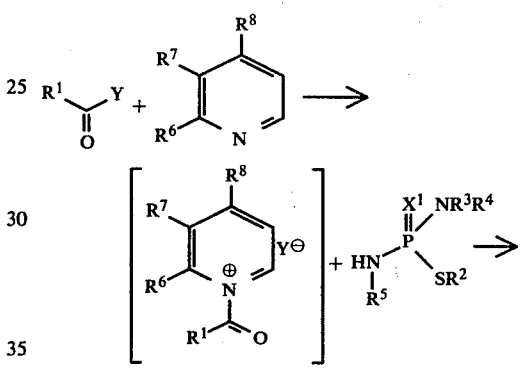

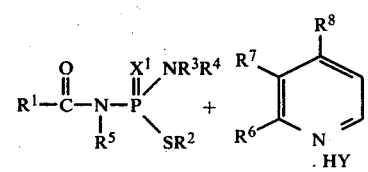

wherein
R$^1$, R$^2$, R$^3$, R$^4$, R$^5$ and X are as defined for Formula I and R$^6$ and R$^7$ are hydrogen, or together form the "B" ring of quinoline;

R$^7$ and R$^8$ together form the "B" ring of isoquinoline; or

R$^8$ is hydrogen, amino, mono or di(C$_1$–C$_6$)alkylamino, or a nitrogen containing (C$_2$–C$_6$) heterocyclic ring bonded at N; when R$^8$ is not a member of the B ring of isoquinoline; and Y is chlorine or bromine.

A commonly assigned application, simultaneously filed, Ser. No. 102,472 describes more fully this aspect of the invention and is hereby incorporated by reference.

The N'-mono- or di-alkyl N-alkyl or substituted alkyl S-alkyl phosphorodiamidothioate intermediates can be prepared in one or two steps by the reaction of an S-alkyl phosphorodichloridothioate with monoalkyl or dialkyl amines.

When the two amine groups are different, the S-alkyl phosphorodichloridothioate is reacted with one of the amine groups to form a monochloride intermediate. The second amine group is then added.

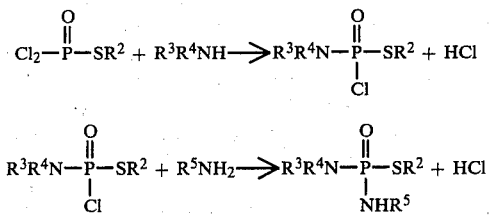

When R$^3$ and R$^5$ are the same (C$_1$–C$_3$) monoalkyl, the intermediates are formed by adding two moles of amine to the S-alkyl phosphorodichloridothioate.

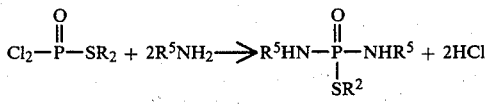

The above reactions are preferably carried out in the presence of an acid binding reagent, such as a dialkylaniline, pyridine or trialkyl amine. Two additional moles of R$^5$NH$_2$ may serve as the acid binding agent when R$^5$NH$_2$ is the reactant.

For preparation of both intermediate and acyl phosphorodiamidothioates, generally a substantially equimolar ratio of reactants is preferred. While not required, the reaction is advantageously carried out in the presence of an inert organic solvent such as an ether, aromatic hydrocarbon, halogenated aromatic hydrocarbon, aliphatic hydrocarbon, aliphatic nitrile, nitroalkyl or nitroaryl and the like, or mixtures thereof. Suitable solvents include, for example, ethyl ether, dioxane, methylene chloride, tetrahydrofuran, benzene, toluene, chlorobenzene, heptane, acetonitrile, nitromethane, nitrobenzene and the like. The reaction is generally conducted in a temperature range of about −10° C. to 100° C. or more, and preferably in the range of about 0° to about 60° C.

All of the starting materials used in the preparation of the compounds of this invention are known compounds, are readily prepared by adaptions of known routes or are herein described. For example, the formamidine starting materials are prepared by condensation of an aniline with an N-alkyl formamide. (U.S. Pat. No. 3,502,720, Belgian Pat. No. 771,792, South African Pat. No. 732,129.)

The following examples are given by way of illustration, and are not to be considered as limitations of the present invention.

EXAMPLE 1

N,N'-Dimethyl S-(1-methylpropyl) phosphorodiamidothioate

Excess methylamine is bubbled into an ice-cooled solution of S-(1-methylpropyl) phosphorodichloridothioate 11 g (0.054 mole), in 50 ml of tetrahydrofuran (THF). The reaction is stirred ½ hour at room temperature, diluted with 200 ml of ether, filtered to remove the methylamine hydrochloride, and evaporated to give 10 g (94% of theory) of product as an orange oil.

EXAMPLE 2

N,N'-Dimethyl S-(2-methylpropyl) phosphorodiamidothioate

Excess methylamine is bubbled into a solution of S-(2-methylpropyl) phosphorodichloridothioate, 50 g (0.24 mole), in 300 ml of ether. The reaction is stirred 2½ hrs. at room temperature and filtered. The ether solution is washed with 100 ml of water, dried over 4A molecular sieves, and evaporated to an oil. The water wash is saturated with sodium chloride and extracted with ether.

This ether solution is dried over 4Å molecular sieves and dried to an oil. The two oils are combined, yielding 41 g. (85% of theory).

The following intermediates are prepared in an analogous manner.

EXAMPLE 3

N,N'-Diethyl S-propyl phosphorodiamidothioate

EXAMPLE 4

N,N'-Diethyl S-(1-methylpropyl) phosphorodiamidothioate

EXAMPLE 5

S-(1-Methylpropyl) N,N'-(2-propenyl)phosphorodiamidothioate

EXAMPLE 6

S-(1-Methylpropyl) N,N'-dipropyl phosphorodiamidothioate

EXAMPLE 7

N,N'-Dimethyl S-(1-methylethyl)phosphorodiamidothioate

EXAMPLE 8

N,N',N'-Trimethyl S-(1-methylpropyl)phosphorodiamidothioate

A solution of dimethylamine, 5.8 g (0.13 mole), and triethylamine, 13.0 g. (0.13 mole), in 100 ml of THF is added dropwise to an ice-cooled solution of S-(1-methylpropyl) phosphorodichloridothioate, 27 g. (0.13 mole), in 200 ml of THF. The reaction is stirred 1 hour at room temperature. A solution of methylamine, 3.96 g. (0.13 mole), and triethylamine, 13.0 g. (0.13 mole), is added at ice-bath temperature. The reaction is stirred 2 hours at room temperature and stands overnight. The triethylamine hydrochloride is filtered and the THF is evaporated. Ether, 150 ml, and hexane, 100 ml are added, precipitating more triethylamine hydrochloride. The suspension is filtered through Super-Cel and the solvents are evaporated to give 26 g. (95% of theory) of oil.

Example 9 is prepared in an analogous manner.

EXAMPLE 9

N,N'N'-Trimethyl S-propyl phosphorodiamidothioate

N-Acyl Phosphorodiamidothioate Products

EXAMPLE 10

N-Hydrogencarbonyl N,N'-dimethyl S-(1-methylpropyl) phosphorodiamidothioate

Formic acid, 10 ml, and acetic anhydride, 20 ml, are mixed at room temperature and heated at 50° for 15 minutes, then recooled in ice. A solution of N,N'-dimethyl S-(1-methylpropyl) phosphorodiamidothioate, 39.2 g. (0.2 mole), and 0.5 ml of 85% phosphoric acid in 30 ml of methylene chloride are added. The solution is warmed to room temperature and stirred 6 days at room temperature. One half of the mixture is diluted in 100 ml of $CH_2Cl_2$ and extracted with three 100 ml portions of water. The methylene chloride is dried over 4Å molecular sieves, filtered, and evaporated to give 12 g. (50% yield) of product as an oil.

Th following compounds are prepared in a manner analogous to Example 10.

EXAMPLE 11

N-Hydrogencarbonyl N,N',N'-trimethyl S-(1-methylpropyl) phosphorodiamidothioate

EXAMPLE 12

N-Hydrogencarbonyl N,N'-dimethyl S-(2-methylpropyl) phosphorodiamidothioate

EXAMPLE 13

N-Hydrogencarbonyl N,N'-dimethyl S-propyl phosphorodiamidothioate

EXAMPLE 14

N-Hydrogencarbonyl N,N'-di(2-propenyl) S-(1-methylpropyl) phosphorodiamidothioate

EXAMPLE 15

N,N'-Diethyl N-hydrogencarbonyl S-(1-methylpropyl) phosphorodiamidothioate

EXAMPLE 16

N,N'-Diethyl N-hydrogencarbonyl S-propyl phosphorodiamidothioate

EXAMPLE 17

N-Hydrogencarbonyl N,N',N'-trimethyl S-propyl phosphorodiamidothioate

EXAMPLE 18

N-Hydrogencarbonyl N,N'-dimethyl S-(1-methylethyl) phosphorodiamidothioate

EXAMPLE 19

N-Hydrogencarbonyl N,N'-dimethyl S-(3-methylbutyl) phosphorodiamidothioate

EXAMPLE 20

S-Ethyl N-hydrogencarbonyl N,N'-dimethyl phosphorodiamidothioate

EXAMPLE 21

N-Ethyl N-hydrogencarbonyl N'-methyl S-(1-methylpropyl) phosphorodiamidothioate

N-Ethyl N'-methyl N-[(4-methylphenylimino)methyl] S-(1-methylpropyl) phosphorodiamidothioate is hydrolyzed as 5% active ingredient on Celatom MP-78 granular, which has a pH of 5 and contains 3% water, over two to six weeks. The organic compounds are extracted by stirring 200 g. of the 5% Celatom granular in 1200 ml of toluene for 3 mins. The solvent is filtered through Super-Cel and evaporated to give 6.7 g of oil. The product is isolated and purified by preparative liquid chromatography used two PrepPak-500 silica gel columns in series and a mobile phase of 90 ethyl acetate/10 isooctane at a flow rate of 250 ml/min. Recovery of product is 2.9 g.

EXAMPLE 22A

N,N'-Dimethyl N-methylcarbonyl S-(1-methylpropyl) phosphorodiamidothioate

N,N'-Dimethyl S-(1-methylpropyl) phosphorodiamidothioate, 7.1 g. (0.036 mole), acetic anhydride, 7.44 g. (0.073 mole), and 0.1 ml of 85% phosphoric acid are heated for 9 hours at reflux in 10 ml of methylene chloride. The mixture is extracted with two 50 ml portions of water, dried with 4Å molecular sieves, and evaporated to give 7 g. of oil. The product is purified by column chromatography on 20 g. of Biosil A. Elution with toluene (3×100 ml portions) and 1/1 ether hexane (250 ml) gives 0.7 g. (8% yield) of product as an oil.

EXAMPLE 22B

N,N'-Dimethyl N-methylcarbonyl S-(1-methylpropyl) phosphorodiamidothioate

Aluminum chloride, 7.0 g. (0.052 moles), is dissolved in 30 ml. of nitromethane which has been dried over 4A molecular sieves. The reaction exotherms to 35°, and is cooled to room temperature. Acetyl chloride, 3.8 ml. (0.052 mole), is added and the reaction is stirred 10 min. at room temperature. A solution of N,N'-dimethyl S-(1-methylpropyl) phosphorodiamidothioate, 5 g (0.026 mole), in 20 ml. of nitromethane is added and stirring is continued for 8 hr. at room temperature. After standing overnight, the reaction is diluted with 100 ml. of ether, extracted with 50 of water, then 5% sodium bicarbonate solution. The ether layer is dried over 4Å molecular sieves, filtered, and evaporated to yield 2.6 g. (40% of theory) of product as a yellow oil.

EXAMPLE 23

N,N'-Dimethyl S-(1-methylpropyl) N-trifluoromethylcarbonyl phosphorodiamidothioate N,N'-Dimethyl S-(1-methylpropyl) phosphorodiamidothioate, 15 g (0.08 mole), trifluoroacetic anhydride, 25.2 g (0.12 mole) 0.2 ml of 85% $H_3PO_4$ and 20 ml of methylene chloride are heated 7 hours at reflux. The reaction is extracted with 100 ml of water, dried over 4A molecular sieves, heated, and evaporated to give 19.2 g of oil. Purification of 10 g. of material by preparative high pressure liquid chromatography using two PrepPak 500 silica gel columns in series and a mobile phase of 70 ethyl acetate/30 isooctane gives 2 g of product.

EXAMPLE 24A

N'N'-Dimethyl S-(1-methylpropyl) N-nonylcarbonyl phosphorodiamidothioate

A solution of N,N'-dimethyl S-(1-methylpropyl) phosphorodiamidothioate, 10.6 g. (0.054 mole), and pyridine, 4.3 g. (0.054 mole), in 40 ml of toluene is added to an ice-cooled solution of decanoyl chloride, 10.3 g. (0.054 mole), in 50 ml of toluene. A white solid formed after a few minutes. The suspension is stirred 4 days at ambient temperature. It is extracted sequentially with 250 ml of 5% sodium bicarbonate and 2% hydrochloric acid. The organic layer is dried with 4A molecular sieves, evaporated to give 15 g. of yellow oil. Chromatography on 60 g. of Biosil A (elution with 10% ether in toluene) gives 3 g. (17% yield) of product. B) A solution of N,N'-dimethyl S-(1-methylpropyl) phosphorodiamidothioate, 5.3 g. (0.026 mole), and 4-pyrrolidinopyridine, 3.80 g. (0.026 mole), in 20 ml of toluene is added dropwise over 10 min. to an ice-cooled solution of decanoyl chloride, 5.13 g. (0.026 mole), in 25 ml of toluene, maintaining a temperature of 10°–13° C., for ½ hr. after completion of addition. The reaction is stirred 24 hrs., diluted with 100 ml of ether, filtered, and evaporated to give 8.4 g. of crude product. The spectral data (nmr and ir) were similar to those of Method A.

The following examples are prepared in a manner analogous to 24A.

EXAMPLE 25

N,N'-Dimethyl S-(1-methylpropyl) N-(4-nitrophenyl) carbonyl phosphorodiamidothioate

EXAMPLE 26

N-[(2-Methoxycarbonyl)ethyl carbonyl] N,N'-dimethyl S-(1-methylpropyl) phosphoro-diamidothioate

EXAMPLE 27

N-Methoxymethylcarbonyl N,N'-dimethyl S-(1-methylpropyl) phosphorodiamidothioate

EXAMPLE 28

N-Dichloromethylcarbonyl N,N'-dimethyl S-(1-methylpropyl) phosphorodiamidothioate

EXAMPLE 29

N-[(1-Bromoethyl)carbonyl] N',N'-dimethyl S-(1-methylpropyl) phosphorodiamidothioate

EXAMPLE 30

N-[(1-Chloroethyl)carbonyl] N,N'-dimethyl S-(1-methylpropyl) phosphorodiamidothioate

EXAMPLE 31

N,N'-Dimethyl S-(1-methylpropyl) N-phenylcarbonyl phosphorodiamidothioate

EXAMPLE 32

N,N'-Dimethyl S-(1-methylpropyl) N-[(2-phenylethylene) carbonyl]phosphorodiamidothioate

EXAMPLE 33

N-Chloromethyl carbonyl N,N'-dimethyl S-(1-methyl-propyl) phosphorodiamidothioate

EXAMPLE 34

N-Bromomethylcarbonyl N,N'-dimethyl S-(1-methylpropyl) phosphorodiamidothioate

EXAMPLE 35

N-[(Ethoxycarbonylmethyl)carbonyl] N,N'-dimethyl S-(1-methylpropyl) phosphorodiamidothioate

EXAMPLE 36

N-Cyclopropylcarbonyl N,N'-dimethyl S-(1-methylpropyl) phosphorodiamidothioate

EXAMPLE 37

N-(Methoxycarbonyl)carbonyl N,N'-dimethyl S-(1-methylpropyl) phosphorodiamidothioate A solution of N,N'-dimethyl S-(1-methylpropyl) phosphorodiamidothioate, 10 g. (0.051 moles), and pyridine, 8.1 g. (0.102 moles), in 50 ml of toluene is added dropwise to an ice-cooled solution of methyl oxalyl chloride, 12.5 g. (0.102 moles), in 50 ml. of toluene. The mixture is stirred 48 hr. at room temperature, filtered to remove the pyridine hydrochloride, and evaporated. The residual oil is diluted with 200 ml of ether, precipitating additional pyridine hydrochloride, filtered, and evaporated to give 11 g. of oil. Purification by preparative high pressure liquid chromatography using one PrepPak 500 silica gel column and a mobile phase of ethyl acetate gives 2.0 g. (14% of theory) of product.

The following examples are prepared in an analogous manner.

EXAMPLE 38

N-(3-Chloropropyl)carbonyl N,N'-dimethyl S-(1-methylpropyl) phosphorodiamidothioate

EXAMPLE 39

N-(8,11-Heptadecadienyl)carbonyl N,N'-dimethyl S-(1-methylpropyl) phosphorodiamidothioate

EXAMPLE 40

N,N'-Dimethyl N-(1-propenecarbonyl) S-(1-methylpropyl) phosphorodiamidothioate

EXAMPLE 41

N,N'-Dimethyl N-(phenylmethyl)carbonyl S-(1-methylpropyl) phosphorodiamidothioate

EXAMPLE 42

N-(4-Chlorophenyl)carbonyl N,N'-dimethyl S-(1-methylpropyl) phosphorodiamidothioate

EXAMPLE 43

N-(2,4-Dichlorophenyl)carbonyl N,N'-dimethyl S-(1-methylpropyl) phosphorodiamidothioate

EXAMPLE 44

N-Cyclohexylcarbonyl N,N'-dimethyl S-(1-methylpropyl) phosphorodiamidothioate

EXAMPLE 45

N,N'-Dimethyl S-(1-methylpropyl) N-(phenoxymethyl)carbonyl phosphorodiamidothioate

EXAMPLE 46

N-(2-Bromoethyl) N,N'-dimethyl S-(1-methylpropyl) phosphorodiamidothioate

EXAMPLE 47

N-Hydrogenthiocarbonyl N,N'-dimethyl S-(1-methylpropyl) phosphorodiamidothioate

Phosphorous pentasulfide, 17.8 g. (0.08 moles) is added to a solution of N-hydrogencarbonyl N,N'-dimethyl S-(1-methylpropyl) phosphorodiamidothioate in 200 ml. of pyridine. The reaction exotherms to 55° C. After stirring 24 hr. at room temperature the mixture is diluted with 300 ml. of ether and filtered through a 5 g. of Biosil A. Evaporation of the solvent gives 3.1 g. of oil. Purification by high pressure liquid chromatography using one PrepPak 500 silica gel column and a mobile phase of 70/30 ethyl acetate/isooctane gives 3 g. of product (25% of theory).

EXAMPLE 48

N-Hydrogencarbonyl N,N'-Dimethyl S-(1-methylpropyl) phosphorodiamidodithioate

Acetic anhydride, 1.76 g. (0.017 mole), is added to a solution of N,N'-dimethyl S-(1-methylpropyl) phosphorodiamidothioate, 3.0 g. (0.014 moles) and formic acid, 0.69 g. (0.015 moles), in 20 ml. of methylene chloride. After 7 days at room temperature, 1.76 g. of acetic anhydride and 0.69 g. of formic acid are added. After an additional 3 days at room temperature the reaction mixture is concentrated, diluted with 50 ml of chloroform, extracted with thre 20 ml portions of 5% sodium bicarbonate, dried over 4Å molecular sieves, filtered, and evaporated to give 2.8 g. (83% of theory) of product. The following example is prepared in an analagous manner.

EXAMPLE 49

N-Hydrogencarbonyl N,N'-dimethyl S-propyl phosphorodiamidodithioate

TABLE I

Elemental Analysis

| Ex. | Emp. Formula | Elemental Analysis Calcd. (Found) | | |
|---|---|---|---|---|
| | | C | H | N |
| 1 | $C_6H_{17}N_2OPS$ | 36.73(36.43) | 8.67(9.02) | 14.28(14.09) |
| 2 | $C_6H_{17}N_2OPS$ | 36.73(36.32) | 8.67(8.83) | 14.28(14.04) |
| 3 | $C_7H_{19}N_2OPS$ | 39.98(39.41) | 9.10(9.35) | 13.32(12.77) |
| 4 | | not available | | |
| 5 | | not available | | |
| 6 | | not available | | |
| 7 | $C_5H_{15}N_2OPS$ | 32.96(32.61) | 8.24(8.23) | 15.38(15.40) |
| 8 | $C_8H_{19}N_2OPS$ | 43.24(41.00) | 8.55(8.65) | 12.61(10.10) |
| 9 | | not available | | |
| 10 | $C_7H_{17}N_2O_2PS$ | 37.50(38.21) | 7.58(7.93) | 12.50(12.52) |
| 11 | $C_8H_{19}N_2O_2PS$ | 40.33(40.98) | 7.98(8.65) | 11.76(10.05) |
| 12 | $C_7H_{17}N_2O_2PS$ | 37.50(37.30) | 7.58(7.94) | 12.50(12.50) |
| 13 | $C_6H_{15}N_2O_2PS$ | 34.28(34.83) | 7.19(7.51) | 13.33(13.53) |
| 14 | $C_{11}H_{21}N_2O_2PS$ | 47.82(46.11) | 7.60(7.63) | 10.14(10.08) |
| 15 | $C_9H_{21}N_2O_2PS$ | 42.85(41.81) | 8.33(8.41) | 11.11(11.92) |
| 16 | $C_8H_{19}N_2OPS$ | 40.33(39.66) | 7.98(8.25) | 11.76(10.82) |
| 17 | $C_7H_{17}N_2O_2PS$ | 37.50(35.55) | 7.58(7.60) | 12.50(12.89) |
| 18 | $C_6H_{15}N_2O_2PS$ | 34.28(35.05) | 7.19(7.19) | 13.33(14.55) |
| 19 | $C_8H_{19}N_2OPS$ | 40.33(40.79) | 7.98(8.50) | 11.76(11.94) |
| 20 | $C_5H_{13}N_2O_2PS$ | 30.76(31.04) | 6.66(6.65) | 14.35(14.08) |
| 21 | $C_8H_{19}N_2O_2PS$ | 40.33(40.38) | 7.98(8.12) | 11.76(11.94) |
| 22 | $C_8H_{19}N_2O_2PS$ | 40.33(39.52) | 7.98(8.61) | 11.76(11.98) |
| 23 | $C_8H_{16}F_3N_2O_2PS$ | 32.87(31.98) | 5.47(5.34) | 9.58(9.60) |
| 24 | $C_{16}H_{25}N_2O_2PS$ | 56.47(55.44) | 7.35(7.97) | 8.23(10.42) |
| 25 | $C_{13}H_{20}N_3O_4PS$ | 45.21(45.34) | 5.79(5.94) | 12.17(12.19) |
| 26 | $C_{11}H_{23}N_2O_4PS$ | 39.05(38.43) | 6.80(6.08) | 8.23(10.81) |
| 27 | $C_9H_{21}N_2O_3PS$ | 40.29(40.57) | 7.83(7.90) | 10.44(9.84) |
| 28 | $C_8H_{17}N_2Cl_2O_2PS$ | 31.27(32.10) | 5.58(5.40) | 9.12(8.40) |
| 29 | $C_9H_{20}N_2BrN_2O_2PS$ | 32.62(36.00) | 6.04(6.98) | 8.46(8.97) |
| 30 | $C_9H_{20}N_2ClO_2PS$ | 37.69(40.27) | 6.98(7.33) | 9.77(11.44) |
| 31 | $C_{13}H_{21}N_2O_4PS$ | 52.00(56.58) | 7.05(7.23) | 9.32(9.74) |
| 32 | $C_{15}H_{23}N_2O_2PS$ | 55.21(55.42) | 7.10(7.64) | 8.58(8.41) |
| 33 | $C_8H_{18}N_2ClO_2PS$ | 35.33(35.21) | 6.65(6.85) | 10.28(9.81) |

TABLE I-continued

Elemental Analysis

| 34 | $C_8H_{18}BrN_2O_2PS$ | 30.29(30.54) | 5.71(6.17) | 8.83(8.79) |
|---|---|---|---|---|
| 35 | $C_{11}H_{23}N_2O_4PS$ | 42.58(42.35) | 7.47(7.64) | 9.03(9.21) |
| 36 | $C_{10}H_{21}N_2O_2PS$ | 45.45(45.27) | 8.01(8.15) | 10.59(10.49) |
| 37 | $C_9H_{19}N_2O_4PS$ | 38.30(33.15) | 6.78(6.21) | 9.92(10.72) |
| 38 | $C_{10}H_{22}ClN_2O_2PS$ | 39.93(39.92) | 7.37(7.74) | 9.31(9.63) |
| 39 | $C_{24}H_{47}N_2O_2PS$ | 62.88(62.32) | 10.26(10.79) | 6.10(6.31) |
| 40 | $C_{10}H_{21}N_2O_2PS$ | 45.45(46.18) | 8.01(8.10) | 10.60(10.40) |
| 41 | $C_{19}H_{23}N_2O_2PS$ | 53.50(53.79) | 7.37(7.59) | 8.91(8.77) |
| 42 | $C_{13}H_{20}N_2ClO_2PS$ | 46.59(45.78) | 6.02(5.94) | 8.37(7.87) |
| 43 | $C_{13}H_{19}Cl_2N_2O_2PS$ | 42.28(42.65) | 5.19(7.79) | 7.59(10.48) |
| 44 | $C_{13}H_{27}N_2O_2PS$ | 50.98(50.24) | 8.88(9.27) | 9.14(9.09) |
| 45 | $C_{14}H_{23}N_2O_3PS$ | 50.91(50.83) | 7.00(7.29) | 8.50(8.25) |
| 46 | $C_9H_{20}BrN_2O_2PS$ | 32.62(36.00) | 6.10(6.98) | 8.40(8.97) |
| 47 | $C_7H_{17}N_2OPS_2$ | 35.00(35.25) | 7.08(7.55) | 11.70(12.22) |
| 48 | $C_7H_{17}N_2OPS_2$ | 35.00(35.30) | 7.08(7.22) | 11.70(11.47) |
| 49 | $C_6H_{15}N_2OPS_2$ | 31.80(31.57) | 6.68(6.90) | 12.38(12.01) |

Initial evaluations are made on the following mite, insect, and nematode:

| Code Symbol | Common Name | Latin Name |
|---|---|---|
| TSM | Two-spotted spider mite | *Tetranychus urticae* |
| SAW | Southern armyworm | *Spodoptera eridania* |
| nema | Southern root-knot nematode | *Meloidogyne incognita* |

A test solution containing 600 ppm of test compound can be made by dissolving the test compound in a solvent (acetone:methanol, 1:1), adding surfactant and then water to give an acetone:methanol:water system of 10:10:80. A 1:1 mixture of an alkylarylpolyetheralcohol (commercially available under the trademark Triton X-155) and a modified phthalic glycerol alkyl resin (commercially available under the trademark Triton B-1956) can be utilized at the equivalent of one ounce per 100 gallons of test solution and a surfactant.

For the mite test, infested bean (*Phaseolus limeanus*) leaf discs (1.25 inches in diameter) containing about 50 mites are placed in a Petri dish lid on a moistened piece of cotton. The leaves are then sprayed with the test solution using a rotating turntable. They are held for 24 hours and then the percent kill is determined.

For the armyworm test, detached bean leaves on pieces of moistened filter paper are sprayed as above for the mite test in similar dishes and allowed to dry. The dishes are infested with 10 third instar southern armyworm larvae. The dishes are covered. After holding for 48 hours, the percent kill is obtained.

For the nematode test, soil is homogeneously inoculated with a macerated blend of tomato roots heavily knotted with the root knot nematode. Ten milliliters of the test solution are added to 200 milliliters of the inoculated soil in a 16 oz. jar to give a concentration by volume of about 30 ppm. The jar is then shaken to insure thorough mixing, immediately uncapped, and allowed to air for 24 hours. The soil is then placed into a 3 inch plastic pot after which time 3 cucumber (*Cucumis sativus*) seeds are planted. About 23 days thereafter, the cucumber plants are removed from the soil and the root system examined for the presence of knots. A total of 15 knots or less is considered as a measure of control.

Table II gives the results of the foregoing biological evaluations.

TABLE II

| | Screening Results, % Control[b] | | |
|---|---|---|---|
| Example # | TSM[a] | SAW[a] | NEMA[c] |
| 1 | 100 | 100 | + |
| 2 | 100 | 100 | + |

TABLE II-continued

| Example # | Screening Results, % Control[b] | | |
|---|---|---|---|
| | TSM[a] | SAW[a] | NEMA[c] |
| 3 | 100 | 100 | + |
| 4 | — | — | — |
| 5 | — | — | — |
| 6 | — | — | — |
| 7 | 100 | 0 | + |
| 8 | — | — | — |
| 9 | — | — | — |
| 10 | 100 | 100 | + |
| 11 | 100 | 100 | + |
| 12 | 100 | 100 | + |
| 13 | 100 | 100 | + |
| 14 | 100 | 100 | + |
| 15 | 100 | 100 | + |
| 16 | 100 | 100 | + |
| 17 | 100 | 100 | + |
| 18 | 100 | 100 | + |
| 19 | 100 | 100 | + |
| 20 | 100 | 100 | + |
| 21 | 100 | 100 | — |
| 22 | 100 | 100 | + |
| 23 | 100 | 100 | + |
| 24 | 100 | 100 | + |
| 25 | 100 | 100 | + |
| 26 | 100 | 40 | + |
| 27 | 100 | 100 | + |
| 28 | 100 | 100 | + |
| 29 | 100 | 100 | + |
| 30 | 100 | 100 | + |
| 31 | 100 | 100 | + |
| 32 | 100 | 100 | + |
| 33 | 100 | 100 | + |
| 34 | 100 | 100 | + |
| 35 | 0 | 0 | — |
| 36 | 100 | 100 | + |
| 37 | 0 | 0 | — |
| 38 | 100 | 100 | + |
| 39 | 100 | 0 | + |
| 40 | 100 | 100 | + |
| 41 | 100 | 100 | + |
| 42 | 100 | 100 | + |
| 43 | 100 | 100 | + |
| 44 | 100 | 100 | + |
| 45 | 100 | 100 | + |
| 46 | 100 | 100 | + |
| 47 | 100 | 100 | + |
| 48 | 100 | 100 | + |
| 49 | 100 | 100 | + |

[a]TSM = two-spotted mite; SAW = southern armyworm; nema = nematode.
[b]Insecticidal screening results; % control at 600 ppm
[c]+ means control 15 knots or less (at 30 ppm in soil)
*Examples 4, 5, 6, 8 and 9 are intermediate compounds for which no biological data is included.

The compounds of the invention are useful for the protection of plants and animals, including mammals, from the ravages of harmful and annoying pests. These compounds are particularly effective against arthropods (in varying stages of development) and are especially effective against members of the Class Arachnoidea, which includes the Order Acarina, as represented by mites and ticks, and the Class Insecta, the insects. Among the arthropods which are effectively controlled by the compounds of the present invention are the chewing insects, e.g., the southern armyworm (*Spodoptera eridania*), mites, e.g., the two-spotted spider mite (*Tetranychus urticae*) and others.

The compounds of this invention are also active as fungicides.

Furthermore, compounds of this invention possess nematocidal activity. Among the nematodes which are effectively controlled by the compounds of the present invention are soil nematodes, typified by the southern root knot nematode (*Meloidogyne incognita*).

Generally, control of pests is achieved in accordance with this invention by application of the compounds in pesticidally effective amounts (e.g., arthropodicidally effective amounts) either directly to the pests to be controlled or to the loci to be freed of or protected from attack by such pests. Plant protection loci may be defined as the aerial and subterranean portions of plants or propagative subunits and their immediate or future environs. For example, food, fiber, forage, forest, and ornamental crops and stored products thereof represent plant protection loci. Treatment with compounds of this invention of domestic animals, and their immediate environs similarly constitute representative loci for protection against various annoying ectoparasitic or endoparasitic Acarina (Acari) and Insecta. Many of the below formulations can be utilized on animals in the control of parasites. Thus, the compounds can be deposited on or in the soil, plants, insects, manmade structures, or other substrates as deposits, coatings, etc. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of a living organism. Such means can comprise a complete killing action, eradication, arresting in growth, inhibition, reduction in number or any combination thereof.

The term "pest" as employed in the specification and claims of this application refers to fungi, nematodes and various arthropods especially insects and acarids.

The phosphorodiamidothioates of this invention possess general utility as arthropodicites, particularly as against members of the class Arachnoidea, which includes the order Acarina, as represented by mites and ticks, and Insecta, the insects. Certain compounds of this invention are also active as nematocides and fungicides, particularly nematocides.

FORMULATIONS

For use as pesticides, the compounds of this invention can be used as solutions in organic solvents or formulations. For example, they can be formulated as wettable powders, emulsifiable concentrates, dusts, granular formulations or flowable emulsifiable concentrates. In such formulations, the phosphorodiamidothioates are extended with an agronomically acceptable liquid or solid carrier and, when desired, suitable surfactants are likewise incorporated. Surfactants commonly used in the art can be found in the John W. McCutcheon, Inc. publication "Detergents and Emulsifiers Annual".

The phosphorodiamidothioates can be taken up or mixed with a finely particled solid carrier, as for example, clays, inorganic silicates, carbonates, and silicas. Organic carriers can also be employed. Dust concentrates are commonly made wherein phosphorodiamidothioates are present in the range of about 20 to about 80%. For ultimate applications, these concentrates are normally extended with additional solid to give an active ingredient content of from about 1 to about 20%. Granular formulations are made using a granular or pelletized form of carrier, such as granular clays, vermiculite, charcoal or corn cobs, and can contain the active ingredient in from about 1 to about 25% by weight.

Wettable powder formulations are made by incorporating the compounds of this invention in an inert, finely divided solid carrier along with a surfactant which can be one or more emulsifying, wetting, dispersing or spreading agents or blend of these. The phosphorodiamidothioates are usually present in the range of about 10 to about 35% by weight and surfactants from about 0.5 to about 10% by weight.

One convenient method for preparing a solid formulation is to impregnate the phosphorodiamidothioate onto the solid carrier by means of a volatile solvent such as acetone. In this manner, adjuvants, such as activators, adhesives, plant nutrients, synergists and various surfactants can also be incorporated.

Emulsifiable concentrate formulations can be prepared by dissolving the phosphororiamidothioates of this invention in an agronomically acceptable organic solvent and adding a solvent-soluble emulsifying agent. Suitable solvents are usually water-immiscible and can be found in the hydrocarbon, ketone, ester, alcohol and amide groups of organic solvents. Mixtures of solvents are commonly employed. The surfactants useful as emulsifying agents can constitute about 0.5 to about 10% by weight of emulsifiable concentrate and can be anionic, cationic or non-ionic in character. The concentration of the active ingredients can vary from about 20 to about 50%.

For use as pesticidal agents, these compounds should be applied in an effective amount sufficient to exert the desired pesticidal activity by techniques well known in the art. Usually, this will involve the application of the phosphorodiamidothioate to the loci to be protected from or freed of pests in an effective amount when incorporated in an agronomically acceptable carrier. However, in certain situations, it may be desirable and advantageous to apply the compounds directly onto the loci to be protected from or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purpose for such application, the phosphorodiamidothioate being utilized, the frequency of dissemination and the like.

By "agronomically acceptable carrier" is meant any substance which can be utilized to dissolve, disperse, or diffuse the chemical incorporated therein without impairing the effectiveness of the toxic agent and which does no permanent damage to such environment as soil, equipment and agronomic crops.

For use as insecticides and acaricides, dilute sprays can be applied at concentrations of about 0.01 to about 20 pounds of the phosphorodiamidothioate ingredient per 100 gallons of spray. They are usually applied at about 0.1 to about 5 pounds per 100 gallons. In more concentrated sprays, the active ingredient is increased by a factor of about 2 to about 12. With dilute sprays, applications are usually made to the plants until run off is achieved, whereas with more concentrated low-volume sprays, the materials are applied as mists.

For use as a fungicide, the compounds of this invention can be applied as fungicidal sprays by methods commonly employed, such as, conventional high-gallonage hydraulic sprays, low-gallonage sprays, air-blast sprays, aerial sprays and dusts. The dilution and rate of application will depend upon the type of equipment employed, the method of application and diseases to be controlled, but the preferred effective amount is usually about 0.1 lb. to about 50 lbs. per acre of the active ingredient.

As a fungicidal seed protectant, the amount of toxicant coated on the seed is usually at a dosage rate of about 0.1 to about 20 ounces per hundred pounds of seed. As a soil fungicide the chemical can be incorporated in the soil or applied to the surface usually at a rate of about 0.1 to about 50 lbs. per acre. As a foliar fungicide, the toxicant is usually applied to growing plants at a rate of about 0.25 to about 10 lbs. per acre.

For use as a nematocide, systemic agent, or as a soil insecticide, the phosphorodiamidothioates can be applied as a solid formulation, preferably a granular formulation or as a diluted liquid preparation, by broadcasting, sidedressing soil incorporation or seed treatment.

The composition can also be added to transplant or irrigation water or to units employed in propagation, such as seeds, tubers, roots, seedlings, etc., so as to disinfect and/or provide residual protection from nematodes, soil insects (and mites) and via systemic uptake, foliar pests. The application rate can be from about 0.5 to about 50 pounds per acre; however, higher rates can also be used. The preferred rate is from about 1 to about 25 pounds per acre. For soil incorporation, the compounds of this invention can be mixed with the soil or other growth medium at a rate of about 1 to about 100 ppm of active ingredient.

The compounds of this invention can be utilized as the sole pesticidal agents or they can be employed in conjunction with other bactericides, fungicides, herbicides, insecticides, acaricides, nematocides and comparable pesticides.

The following are examples of formulations are given by way of illustration, and are not to be considered as limitations of the present invention.

Wettable Powder (a) 10%

10.0% active ingredient
0.5% sodium lauryl sulfate
3.0% sodium lignosulfonate
86.5% Kaolin (particle size 10–50 microns)

(b) 35%

35.0% active ingredient
0.5% sodium lauryl sulfate
3.0% sodium lignosulfonate
20.0% precipitated silica, particle size 1 micron
41.5% Kaolin, particle size 10–50 microns Granulate (a) 1%

1% active ingredient
99% Celatom MP78 (diatomaceous earth)

(b) 25%

25% active ingredient
70% altapulgite
5% pyrogenic silica, particle size 1 micron (spray active ingredient on granule, add pyrogenic silica)

(c) 10%

10% active ingredient
90% Agsorb MB (Montmorillinite clay - Mississippi Brown)

(d) 10%

10% active ingredient
90% corn cob granule (e) 5%

5% active ingredient
95% walnut shell

The above granular formulations can be prepared by either of the two following methods or other suitable means.

The active ingredient is dissolved in 3 parts xylene and this solution is sprayed on the granular material. The xylene is subsequently evaporated.

The active ingredient is dissolved in 4 parts of toluene and this solution is dripped onto granular material in a tumbling jar. The toluene is subsequently evaporated.

Flowable Emulsion Concentrate (a) 20%

20% active ingredient
30% cyclohexane
42% xylene
8% mixture of calcium dodecylbenzenesulfonate and octylphenolethoxylate (b) 50%

50% active ingredient
15% xylene
25% cyclohexanone
10% mixture of calcium dodecylbenzenesulfonate and octylphenolethoxylate Dust Concentrate (a) 10%

10% active ingredient
90% Montmorillonite (b) 20%

20% active ingredient
75% Montmorillonite
5% precipitated silica, particle size 1 micron

TABLE III

| Formulation | % Active Ingredient Concentration | % Preferred Active Ingredient Concentration |
|---|---|---|
| Wettable Powder | 1–35 | 10–35 |
| Emulsifiable Concentrate | 1–50 | 20–50 |
| Flowable Emulsion Concentrate | 1–40 | 20–40 |
| Dust Concentrate | 10–80 | 20–80 |
| Granules | 0.1–25 | 5–15 |

Many variations of this invention are possible without departing from the spirit or scope thereof.

I claim:

1. A compound of the formula:

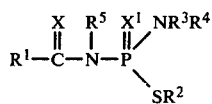

wherein
$R^1$ is a hydrogen atom;
an unsubstituted ($C_1$–$C_6$) alkyl group;
a ($C_1$–$C_6$) alkyl group substituted with up to three substituents selected from fluoro, chloro and bromo groups;
a ($C_1$–$C_6$) alkyl group substituted with one substituent selected from ($C_1$–$C_4$) alkoxy, ($C_1$–$C_4$) alkoxycarbonyl, and phenoxy groups;
a ($C_3$–$C_6$) alkenyl group;
a ($C_4$–$C_{17}$) alkyldienyl group;
a ($C_3$–$C_6$) cycloalkyl group;
a ($C_1$–$C_4$) alkoxycarbonyl group;
an unsubstituted phenyl group;
an unsubstituted phenyl ($C_1$–$C_3$) alkyl group;
an unsubstituted phenyl ($C_2$–$C_6$) alkenyl group;
a phenyl or phenyl ($C_1$–$C_3$) alkyl group; substituted with up to two substituents selected from nitro and chloro groups;
$R^2$ is a ($C_2$–$C_4$) alkyl group;
$R^3$ is a hydrogen atom,
a ($C_1$–$C_3$) alkyl group, or
a ($C_1$–$C_3$) alkenyl group;
$R^4$ is a hydrogen atom or
a ($C_1$–$C_3$) alkyl group;
$R^5$ is a hydrogen atom,
a ($C_1$–$C_3$) alkyl group or
a ($C_1$–$C_3$) alkenyl group; and
X and $X^1$ are an oxygen atom or a sulfur atom.

2. A compound according to claim 1 having the formula:

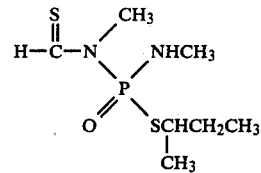

3. A compound according to claim 1 having the formula:

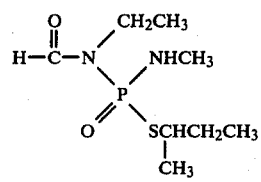

4. A compound according to claim 1 wherein
$R^1$ is a hydrogen atom, a methyl group, an ethyl group, a methoxymethyl group, a cyclopropyl group or a trifluoromethyl group;
$R^5$ is a methyl group; and
X is an oxygen atom.

5. A compound according to claim 4 having the formula:

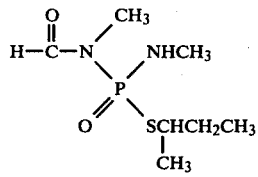

6. A compound according to claim 4 having the formula:

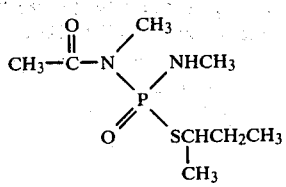

7. A compound according to claim 4 having the formula:

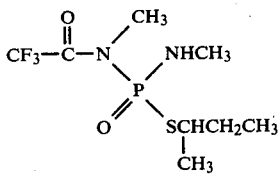

8. A compound according to claim 4 having the formula:

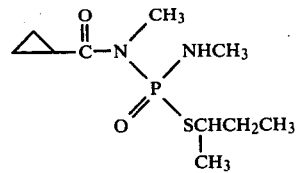

9. A compound according to claim 4 having the formula:

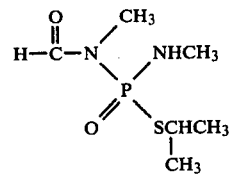

10. A compound according to claim 4 having the formula:

$$\begin{array}{c}O\quad\;CH_3\\ \|\quad/\\H-C-N\quad NHCH_3\\ \;\;\;\;\;\;\;\;\;\;\;\;P\\ \;\;\;\;\;\;\;\;\;O^{\nearrow}\;\;^{\searrow}SCHCH_3\\ \;\;\;\;\;\;\;\;\;\;\;\;\;\;\;\;\;\;\;\;|\\ \;\;\;\;\;\;\;\;\;\;\;\;\;\;\;\;\;\;\;CH_3\end{array}$$

* * * * *